United States Patent [19]
Ramachandran et al.

[11] Patent Number: 5,847,225
[45] Date of Patent: Dec. 8, 1998

[54] PRODUCTION OF NAPHTHYL-SUBSTITUTED KETONES FROM NAPHTHALDEHYDES

[75] Inventors: Venkataraman Ramachandran; Stephen E. Belmont, both of Baton Rouge, La.

[73] Assignee: Albemarle Corporation, Richmond, Va.

[21] Appl. No.: 846,220

[22] Filed: Apr. 25, 1997

[51] Int. Cl.⁶ .................................................. C07C 49/215
[52] U.S. Cl. ............................................ 568/328; 568/313
[58] Field of Search ..................... 568/313, 328

[56] References Cited

U.S. PATENT DOCUMENTS

| | | | |
|---|---|---|---|
| 4,061,779 | 12/1977 | Lake et al. | 424/331 |
| 4,270,004 | 5/1981 | Rose et al. | 568/314 |
| 4,420,639 | 12/1983 | Lake et al. | 568/328 |

FOREIGN PATENT DOCUMENTS

| | | |
|---|---|---|
| 0376516 | 7/1990 | European Pat. Off. . |
| 688207 | 4/1953 | United Kingdom . |

OTHER PUBLICATIONS

Varma et al; Synthetic Commun., 15(4), 279–284 (Abstract only), 1985.

Fieser, Louis F. et al., Organic Chemistry (1944), pp. 700–701.

*Primary Examiner*—Gary Geist
*Assistant Examiner*—Sreen Padmanabhan
*Attorney, Agent, or Firm*—Philip M. Pippenger

[57] ABSTRACT

A mixture formed from 2-naphthaldehyde (e.g., 6-methoxy-2-naphthaldehyde) and a dihydrocarbyl ketone having at least one hydrogen atom in the α-position (e.g., acetone) is heated in the presence of a heterogeneous basic catalyst (e.g., basic alumina) such that the unsaturated 2-naphthyl ketone is formed. The unsaturated ketone can be hydrogenated using, for example, a Pd/C catalyst to form the corresponding saturated ketone. The process enables efficient production of nabumetone and related pharmaceuticals by a clean reaction.

17 Claims, No Drawings

PRODUCTION OF NAPHTHYL-SUBSTITUTED KETONES FROM NAPHTHALDEHYDES

TECHNICAL FIELD

This invention relates to processes for the synthesis of olefinically-unsaturated ketones having naphthyl substituents thereon, and more particularly to the synthesis of aralkenyl alkyl ketones in which the aryl moiety of the aralkenyl group is a substituted 2-naphthyl group and the double bond of the alkenyl moiety of the aralkenyl group is between the $\alpha$ and $\beta$ carbon atoms relative to the carbonyl (keto) group.

BACKGROUND

U.S. Pat. Nos. 4,061,779; 4,270,004; and 4,420,639 describe, inter alia, a class of alkyl aralkyl ketones in which the aryl portion of the aralkyl group is a 2-naphthyl group having a specified substituent in the 6-position. These compounds are reported to have anti-inflammatory and/or analgesic activity, and to have the additional advantage of not excessively irritating the stomach at the therapeutic dose. Among the compounds described in these patents is the well known non-steroidal antiinflammatory agent, 4-(6-methoxy-2-naphthyl)-2-butanone, generally known as nabumetone.

While analogous compounds having a double bond in the aliphatic side chain are also reported in these patents to possess the same beneficial properties, it is further reported in the patent that the carbon-carbon double bond tends to impart a degree of oestrogenicity to these compounds. For this reason, the patent recommends using compounds which do not contain the carbon-carbon double bond. Thus the olefinically unsaturated compounds are hydrogenated to saturate the double bond, and thereby provide superior pharmaceuticals.

In Example 20 of the above patents 4-(6-methoxy-2-naphthyl)-3-buten-2-one is prepared by stirring 6-methoxy-2-naphthalene in excess acetone and aqueous sodium hydroxide, followed by acidification, recovery by ether extraction, and column purification (silica gel column and benzene as eluant). As opposed to the foregoing process in which several co-products are formed in the reaction necessitating tedious separation and purification procedures, it would be highly advantageous if a way could be found for producing 4-(6-methoxy-2-naphthyl)-3-buten-2-one and related substituted 2-naphthyl ketones in an essentially single clean reaction. This invention is deemed to fulfill this need.

SUMMARY OF THE INVENTION

In accordance with this invention there is provided a new, advantageous process for producing 4-(6-methoxy-2-naphthyl)-3-buten-2-one and related aralkenyl alkyl ketones in which the aryl moiety of the aralkenyl group is a substituted 2-naphthyl group and the double bond of the alkenyl moiety of the aralkenyl group is between the $\alpha$ and $\beta$ carbon atoms relative to the carbonyl (keto) group. For ease of reference such products are sometimes referred to hereinafter in the singular as "unsaturated 2-naphthyl ketone" and in the plural as "unsaturated 2-naphthyl ketones" whereas the products formed by hydrogenolysis of the aliphatic double bond are sometimes referred to hereinafter in the singular as "saturated 2-naphthyl ketone" and in the plural as "saturated 2-naphthyl ketones".

It has now been found that if a 2-naphthaldehyde is reacted with a dihydrocarbyl ketone having at least one hydrogen atom in the $\alpha$-position, in the presence of a heterogeneous basic catalyst such as basic alumina, a clean reaction takes place whereby the desired unsaturated 2-naphthyl ketone can be produced in high yield. Moreover, not only is the desired product essentially the only product formed in the reaction, but in addition the catalyst can be readily separated from the product by filtration, centrifugation, decantation, or the like. This in turn facilitates product recovery (if recovery of the unsaturated 2-naphthyl ketone is desired) or subsequent reaction as, for example, hydrogenolysis to form the corresponding saturated 2-naphthyl ketone.

Accordingly, pursuant to one embodiment of this invention there is provided a process for the preparation of an unsaturated 2-naphthyl ketone which comprises mixing a 2-naphthaldehyde with a dihydrocarbyl ketone having at least one hydrogen atom in the $\alpha$-position, and heating the mixture in the presence of a heterogeneous basic catalyst such that the unsaturated 2-naphthyl ketone is formed. If conducted properly, conversions of the 2-naphthaldehyde to unsaturated 2-naphthyl ketone of at least about 80–85 mole % and of a purity of at least about 85–90% (by GC) can be achieved.

Another embodiment of this invention is a process which comprises producing a saturated 2-naphthyl ketone in the manner described in the immediately preceding paragraph, and hydrogenating the olefinic double bond of the unsaturated 2-naphthyl ketone to form the corresponding saturated 2-naphthyl ketone. A preferred method for effecting this selective hydrogenation (i.e., hydrogenation of the olefinic carbon-carbon double bond without excessive hydrogenation of the carbon-oxygen double bond) involves treating the unsaturated 2-naphthyl ketone with hydrogen at atmospheric or slightly elevated pressure (e.g., up to about 100 psi) at one or more temperatures in the range of about 0° to about 100° C., preferably at ambient room temperature, using a palladium/carbon catalyst such as 5% or 10% palladium on charcoal.

These and other embodiments will be still further apparent from the ensuing description and appended claims.

FURTHER DETAILED DESCRIPTION

The preferred unsaturated 2-naphthyl ketones produced in accordance with this invention have the formula:

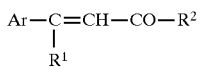

where Ar is an unsubstituted 2-naphthyl group or a substituted 2-naphthyl group where the substitution is in one or more of the 4, 5, 6, 7 and 8 positions, and the substituent or substituents is/are selected from chlorine or bromine atoms, alkoxy groups having 1 to 4 carbon atoms, alkylthio groups having 1 to 4 carbon atoms, and alkyl groups having 1 to 4 carbon atoms; $R^1$ is a hydrogen atom or an alkyl group having up to about 10 carbon atoms, and $R^2$ is a hydrocarbyl group free of olefinic and acetylenic unsaturation and having up to 10 carbon atoms. Preferably, Ar is a monosubstituted 2-naphthyl group in which the substitution is in the 6-position, and most preferably such substituent is a methoxy group. Preferably, $R^1$ is a hydrogen atom or a primary alkyl group, more preferably a hydrogen atom or a methyl group, and most preferably a hydrogen atom. Preferably, $R^2$ is an alkyl group, more preferably a primary alkyl group having 1 to 4 carbon atoms, and most preferably a methyl group.

In the embodiments of this invention wherein the foregoing unsaturated 2-naphthyl ketones are subjected to hydrogenolysis the resultant saturated 2-naphthyl ketones have the formula:

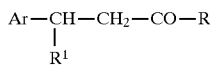

where Ar, $R^1$ and $R^2$ are as described above.

A preferred method for producing the 2-naphthaldehyde or substituted 2-naphthaldehyde (ArCHO, preferably where Ar is as described above) used as the starting material in the process of this invention is to convert an unsubstituted or substituted 2-bromo or 2-chloronaphthalene (ArBr or ArCl, where Ar is as described above) to the Grignard reagent and react dimethylformamide with the Grignard reagent under suitable reaction conditions in accordance with known technology.

The ketone used in the reaction with the 2-naphthaldehyde or substituted 2-naphthaldehyde can be depicted by the formula:

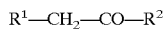

where, preferably, $R^1$ and $R^2$ are as described above. Thus such ketones as acetone, methyl ethyl ketone, diethyl ketone, methyl cyclohexyl ketone, methyl phenyl ketone, methyl cyclopropylcarbinyl ketone, methyl benzyl ketone, etc. can be used. Ketones of the above formula having a boiling point below about 150° C. at 760 mm Hg are preferred, as the excess quantities of such ketones remaining on completion of the reaction can be conveniently removed by reduced pressure distillation. Acetone is the most preferred reactant.

In conducting the reaction between the ketone and the 2-naphthaldehyde or substituted 2-naphthaldehyde, the ketone is usually used in stoichiometric excess, especially when it is a liquid as it thus serves as a convenient medium in which to perform the reaction. If desired, this reaction can be conducted in an ancillary chemically indifferent liquid solvent such as a paraffinic and/or cycloparaffinic hydrocarbon, an ether or polyether, or the like. Temperatures for the reaction typically fall in the range of about 50° to about 120° C., and typically involve reaction periods in the range of about 2 to about 30 hours.

Among suitable heterogeneous basic catalysts for use in the reaction between the ketone and the 2-naphthaldehyde or substituted 2-naphthaldehyde, are acidic substrates such as alumina, beidellite, H-mordenite, or the like, treated with an inorganic base such as the oxides or hydroxides of sodium, potassium, lithium, or calcium. Another type of heterogeneous base that can be used is comprised of certain unsupported inorganic bases of moderate base strength such as calcium hydroxide, a mixture of calcium hydroxide and calcium oxide, potassium carbonate, and like materials. Commercially available basic aluminas which typically are formed by proprietary technology are also attractive candidates for use in the process. One such catalyst is activated, basic, Brockmann I, standard grade, ca. 150 mesh, 58 Å aluminum oxide (Catalog No. 19,944-3, Aldrich 1996–1997 Catalog Handbook of Fine Chemicals), and equivalent materials.

The selective hydrogenation of the carbon-to-carbon double bond in the unsaturated 2-naphthyl ketone is typically performed in a suitable liquid medium such as, for example, ethyl acetate or other liquid lower alkyl ester of acetic or propionic acid; an alkanol such as ethanol, 1-propanol, 2-propanol, 1-butanol, 2-methyl-1-propanol, or the like; or a hydrocarbon such as pentane, hexane heptane, cyclohexane, methylcyclohexane, toluene, one or more xylenes, tetrahydronaphthalene or the like. In some cases a buffer, such as sodium acetate, potassium carbonate or sodium dihydrogen phosphate can be included in the reaction mixture.

The hydrogenation is typically conducted using hydrogen or a suitable hydrogen source such as ammonium formate, (preferably gaseous hydrogen) at atmospheric or elevated pressures (e.g., up to about 2 atmospheres) at one or more temperatures in the range of about 0° to about 60° C., preferably at ambient room temperature. The preferred catalyst is palladium on carbon, such as 5% or 10% palladium on charcoal. Reaction periods typically fall in the range of about 1 to about 15 hours.

The following examples, wherein all percentages are by weight, illustrate the practice and advantages of this invention, and are not to be construed as constituting limitations on the invention.

EXAMPLE 1

4-(6-Methoxy-2-Naphthyl)-But-3-en-2-one

6-Methoxy-2-naphthaldehyde (110 g, 0.591 mol), basic alumina (175 g; Aldrich Chemical Co. Inc.), and acetone (1000 mL) were added to a 2-L 3-neck flask with condenser, mechanical stirrer, and thermocouple attached. The reaction was heated to reflux for 22 hrs, filtered while still hot, and washed with hot ethyl acetate (3×100 mL). The combined organics were concentrated and then put under high vacuum for 24 hours, affording 113.0 g (85%) of 4-(6-methoxy-2-naphthyl)-but-3-en-2-one (93% GC purity). mp 114°–115.5° C.; DSC 114.5° C.; $^1$H NMR (300 MHz, CDCl$_3$) δ 7.80 (s,1H), 7.72–7.55 (m,4H), 7.17–7.08 (m,2H), 6.74 (d,1H, J=10 Hz), 3.89 (s,3H), 2.38 (s,3H); $^{13}$C NMR (75 MHz, CDCl$_3$) δ 198.7, 159.4, 144.1, 136.3, 130.5, 130.2, 129.1, 128.0, 126.7, 124.6, 119.9, 106.5, 55.8, 27.9.

EXAMPLE 2

4-(6-Methoxy-2-Naphthyl)-2-Butanone (via Hydrogenation)

4-(6-Methoxy-2-naphthyl)-but-3-en-2-one (100.0 g, 0.442 mol), (6.0 g), and potassium carbonate (13 g) were slurried in ethyl acetate (1100 mL), stirred 15 minutes, and 5% Pd/C (9.0 g) was added. The flask was purged with H$_2$, a H$_2$ balloon was added, and the reaction was followed by GC. After 12.5 hours, the reaction mass was filtered, washed with H$_2$O (2×150 mL), dried (Na$_2$SO$_4$), filtered, and concentrated in vacuo, affording 95.3 g (95%) of nabumetone (93% purity, 98.5:1.5 ketone:alcohol ratio). The product was recrystallized from EtOH (275 mL) to give 81 g (80%) of 99% nabumetone (92% recovery of contained product). mp 79.5° C.; DSC 81.8° C.; $^1$H NMR (300 MHz, CDCl$_3$) δ 7.61 (d,2H), 7.48 (s,1H), 7.22 (dd,1H), 7.12–7.04 (m,2H); $^{13}$C NMR (75 MHz, CDCl$_3$) δ 208.2, 157.8, 136.6, 133.6, 129.6, 129.4, 128.0, 127.4, 126.7, 119.3, 106.2, 55.7, 45.5, 30.5, 30.2.

The Table summarizes the conditions and results achieved in other hydrogenations of 4-(6-methoxy-2-naphthyl)-but-3-en-2-one formed as in Example 1. All runs were performed at atmospheric pressure. In Runs 1–3 gaseous hydrogen was used. In Runs 4 and 5 the hydrogen source was ammonium formate.

TABLE

| Run | Catalyst | Solvent | Buffer | Reaction Time, Hr | Ketone:Alcohol Ratio |
|---|---|---|---|---|---|
| 1 | 5% Pd/C | EtOH | NaOAc | 4.5 | 94:6 |
| 2 | 5% Pd/C | EtOAc | NaOAc | 3 | 94:6 |
| 3 | 5% Pd/C | Toluene | NaOAc | 2 | 96:4 |
| 4 | 10% Pd/C | EtOAc | None | 43 | 97:3 |
| 5 | 10% Pd/C | EtOH | None | 24 | 95:5 |

The high selectivity of the reaction between the 2-naphthaldehyde and the dihydrocarbyl ketone such as achieved in Example 1 is surprising in light of the mixture of products formed using aqueous sodium hydroxide in Example 20 of U.S. Pat. Nos. 4,061,779; 4,270,004; and 4,420,639. Moreover, a variety of other heterogeneous catalysts have been found relatively ineffective when used in place of the basic alumina used in Example 1. It was found that zeolites and montmorillonites gave no reaction, acidic and basic Amberlyst catalysts and neutral alumina gave moderate activity, while several basic aluminas gave excellent activity.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. In short, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for the preparation of an unsaturated 2-naphthyl ketone which comprises mixing a 2-naphthaldehyde with acetone and heating the mixture in the presence of a heterogeneous basic catalyst such that the unsaturated 2-naphthyl ketone is formed.

2. A process according to claim 1 wherein the 2-naphthaldehyde has the formula, ArCHO, where Ar is an unsubstituted 2-naphthyl group or a substituted 2-naphthyl group where the substitution is in one or more of the 4, 5, 6, 7 and 8 positions, and the substituent or substituents is/are selected from chlorine or bromine atoms, alkoxy groups having 1 to 4 carbon atoms, alkylthio groups having 1 to 4 carbon atoms, and alkyl groups having 1 to 4 carbon atoms.

3. A process according to claim 2 wherein the 2-naphthyl group of said 2-naphthaldehyde is a monosubstituted 2-naphthyl group in which said substitution is in the 6-position.

4. A process according to claim 1 wherein said 2-naphthaldehyde is 6-methoxy-2-naphthaldehyde.

5. A process according to claim 1 wherein said catalyst is a basic alumina catalyst.

6. A process according to claim 2 wherein said catalyst is a basic alumina catalyst.

7. A process according to claim 3 wherein said catalyst is a basic alumina catalyst.

8. A process according to claim 4 wherein said catalyst is a basic alumina catalyst.

9. A process according to claim 1 further comprising hydrogenating the olefinic carbon-to-carbon double bond of said unsaturated 2-naphthyl ketone.

10. A process according to claim 2 further comprising hydrogenating the olefinic carbon-to-carbon double bond of said unsaturated 2-naphthyl ketone.

11. A process according to claim 3 further comprising hydrogenating the olefinic carbon-to-carbon double bond of said unsaturated 2-naphthyl ketone.

12. A process according to claim 4 further comprising hydrogenating the olefinic carbon-to-carbon double bond of said unsaturated 2-naphthyl ketone.

13. A process according to claim 1 wherein the acetone is present in said mixture in stoichiometric excess relative to the 2-naphthaldehyde, and serves as the medium for the reaction between acetone and said 2-naphthaldehyde.

14. A process according to claim 2 wherein the acetone is present in said mixture in stoichiometric excess relative to the 2-naphthaldehyde, and serves as the medium for the reaction between acetone and said 2-naphthaldehyde.

15. A process according to claim 3 wherein the acetone is present in said mixture in stoichiometric excess relative to the 2-naphthaldehyde, and serves as the medium for the reaction between acetone and said 2-naphthaldehyde.

16. A process according to claim 4 wherein the acetone is present in said mixture in stoichiometric excess relative to the 2-naphthaldehyde, and serves as the medium for the reaction between acetone and the 6-methoxy-2-naphthaldehyde.

17. A process according to claim 16 further comprising hydrogenating the olefinic carbon-to-carbon double bond of 4-(6-methoxy-2-naphthyl)-but-3-en-2-one formed in the process to produce 4-(6-methoxy-2-naphthyl)-2-butanone.

* * * * *